United States Patent [19]

Bieringer et al.

[11] Patent Number: 4,483,615

[45] Date of Patent: Nov. 20, 1984

[54] METHOD AND APPARATUS FOR DETECTING CHECKS IN GLASS TUBES

[75] Inventors: Robert J. Bieringer, Toledo, Ohio; Robert D. Kohler, Temperance, Mich.; James A. Ringlien, Maumee, Ohio

[73] Assignee: Owens-Illinois, Inc., Toledo, Ohio

[21] Appl. No.: 332,027

[22] Filed: Dec. 18, 1981

[51] Int. Cl.³ ............................................ G01N 21/88
[52] U.S. Cl. .................................... 356/237; 209/526; 250/572
[58] Field of Search .............. 356/237, 239, 240, 73.1; 209/524, 526, 588; 250/223 B, 214 RC, 563, 572

[56] References Cited

U.S. PATENT DOCUMENTS

| | | | |
|---|---|---|---|
| 3,812,372 | 5/1974 | Wirtz et al. | 250/214 RC X |
| 3,920,970 | 11/1975 | Slaker | 250/572 X |
| 4,136,779 | 1/1979 | Bieringer | 209/524 |
| 4,367,405 | 1/1983 | Ford | 209/526 X |
| 4,378,494 | 3/1983 | Miller | 356/237 |

Primary Examiner—Vincent P. McGraw
Attorney, Agent, or Firm—John R. Nelson; Myron E. Click

[57] ABSTRACT

A method and apparatus for inspecting glass tubes for fire checks and other defects is disclosed. Each tube is positioned on transport equipment and moved through an inspection area as it is rotated about its longitudinal axis by a spinner mechanism. A broad source of diffused light illuminates each tube in the inspection area. A camera is positioned above the moving line of tubes and includes an array of photosensitive diodes arranged parallel to the longitudinal axes of the tubes. A check in a tube will reflect a higher intensity light to the camera than a non-defective portion of the tube. By averaging the signals from the first few diodes for each longitudinal scan of the camera, a reference voltage level can be electronically determined for each scan. Any signal generated by a diode element of the camera which is greater than the sum of the reference signal and a predetermined signal indicates the presence of a defect in the tube.

11 Claims, 4 Drawing Figures

METHOD AND APPARATUS FOR DETECTING CHECKS IN GLASS TUBES

BACKGROUND OF THE INVENTION

1. Field of the Invention

The present invention relates in general to optical inspection devices and in particular to a method and apparatus for optically detecting checks in glass tubes which are being continuously moved through a production machine.

2. Description of the Prior Art

In the manufacture of glass tubes, tubing is cut to achieve a roughly desired length. During the cutoff operation, cracks may occur in the tube. Such cracks usually extend from the cut edge down into the body of the tube. When the ends of the tube are glazed or tooled, the crack may be partially or completely healed. However, if the original crack in the tube extends past the glazed or tooled area, it will remain unhealed as a fire check. Such fire checks are unacceptable defects in the finished glass tube product.

The use of optical scanning devices for inspecting the side walls of glass containers is well known. Numerous devices, such as those shown in U.S. Pat. Nos. 3,708,680 and 3,716,136, have circuitry which includes means for receiving and interpreting light passed through or directed onto an item under inspection. Such devices incorporate either a visual display for comparison of the item or employ a device capable of producing a resistance proportional to the intensity of the light directed thereon. Whether the output of such a device is visual or electrical in nature, it is eventually compared against a model to determine if the item under inspection is suitable as to size and construction and is without flaws, cracks, or foreign objects. Such devices are intended to provide an automated inspection means for checking single or multiple objects, such as in a moving column of bottles.

U.S. Pat. No. 3,877,821 discloses an apparatus having a scanning array which is serially interrogated to generate a train of pulses having amplitudes representing the light transmitted through an object under inspection. Adjacent pulses are compared to generate pulses having amplitudes which represent the difference in pulse amplitudes. The difference pulses can be utilized to indicate a defect in the object being inspected. U.S. Pat. No. 3,942,001 discloses an apparatus for detecting the presence of extraneous matter or cracks in translucent containers. A spot beam of light is projected through the container to generate an inspection signal which is compared with an acceptance signal. The acceptance signal amplitude is varied in accordance with the position of the spot beam with respect to the container.

SUMMARY OF THE INVENTION

The present invention provides an efficient method and apparatus for inspecting glass tubes for fire checks and other defects. Each tube can be placed on a finger type conveyor which includes conventional means for axially rotating the tubes. The conveyor translates the tubes through an inspection area. Thus, each tube is rotated rapidly about its longitudinal axis while being moved in a direction perpendicular to its longitudinal axis through the inspection area.

The inspection area includes a source of diffused light and a diode array camera. The tube is moved over the source of light such that the ends of the tube, where checks may be present, are brightly illuminated. The camera is placed above the moving line of tubes looking down at an angle of approximately 20° F. An array of photosensitive diode elements is arranged parallel to the longitudinal axis of the tube. A lens images the tube being inspected onto the array of diodes. The viewing angle of the camera and the use of tall or wide diodes in the array ensures that the entire exterior surface of the rotating tube will be examined during the passage through the field of the camera.

The light reflected from the diffused source by the cylindrical surface of the tube is generally uniform for each scan of the camera across the region under inspection. However, a check in the tube will reflect more light into the camera producing an increased output singal from the corresponding region of the scan. However, the baseline of the output signal varies greatly in amplitude as the tube passes over the light source. For example, circumferential irregularities in the tubing, light source variations, and camera vibration all can cause changes in the baseline signal. This variation may be greater than a typical output signal caused by a defect. By averaging the signals from the first few diode elements for each camera scan, a reference baseline voltage level can be electronically determined for the remainder of the scan to accommodate interscan variations of the baseline. To account for slight intrascan variations in the response of the diode elements and to provide a sensitivity adjustment, a relatively small predetermined voltage can be added to the reference base line signal. Any voltage generated by a diode element of the camera which is greater than the sum of the reference and predetermined signals indicates the presence of a defect in the inspection area.

It is an object of the present invention to provide an improved method and apparatus for inspecting glass tubes which are being continuously moved through a production machine.

It is another object of the present invention to provide a rapid and efficient means for reliably inspecting for defects the total sidewall of articles moving in combined rotation and translation under normal production conditions.

It is a further object of the present invention to provide an apparatus and a method to enable check detection in glass tubes in the presence of a wide variety of locations and orientations of the tubes.

It is another object of the present invention to provide an apparatus and method for inspecting glass tubes under conditions which present a wide variation in baseline signal levels.

Other objects and advantages of the present invention will become apparent to those skilled in the art from the following detailed description of the preferred embodiment of the invention, when read in light of the accompanying drawings.

DETAILED DESCRIPTION OF THE PREFERRED EMBODIMENT

Figure 1:
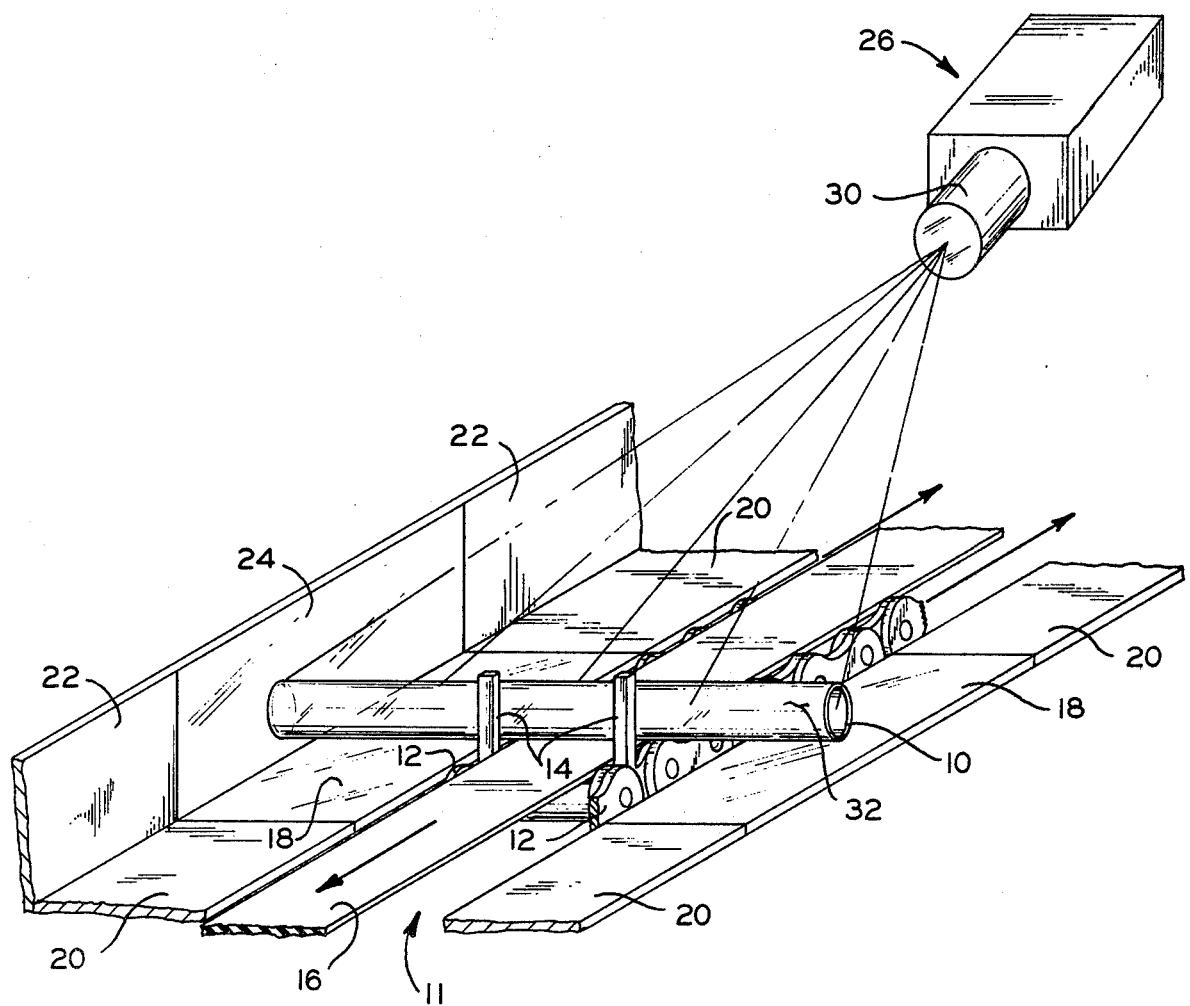
FIG. 1 is a schematic perspective view of a check detector in accordance with the present invention.
Figure 2:
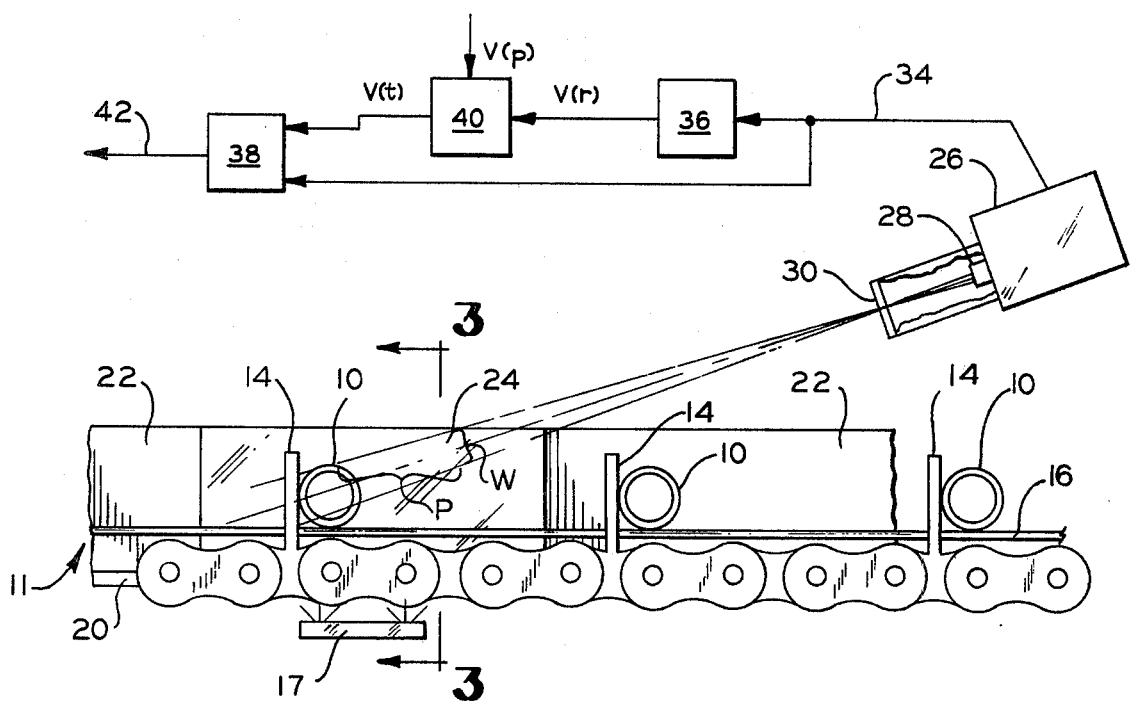
FIG. 2 is a schematic side elevational view of the check detector of FIG. 1.

Referring now to the drawings, there is illustrated in FIGS. 1 and 2 an apparatus for detecting checks in accordance with the present invention. An article to be inspected, such as a cylindrical glass tube 10, is placed on a means for moving or transporting the article through an inspection area. The transport equipment can include a lug type conveyor 11 having a pair of horizontal chains 12 to which are attached vertically extending lugs 14. The conveyor can be a flexible endless belt or chain driven by a conventional motor (not shown) so as to move the lugs 14 and push the tubes 10 through the inspection area. The tubes 10 are supported by and rotated about their longitudinal axes by a rotating mechanism such as a flat belt 16. The flat belt moves rapidly in a direction opposite to the direction of movement of the conveyor chains 12. Thus, each tube is rotated about its longitudinal axis while being moved in a direction perpendicular to its longitudinal axis through the inspection area. These devices are conventional and form no part of the present invention.

Figure 3:
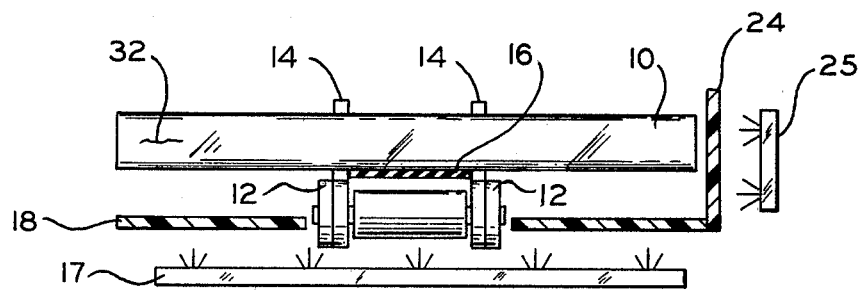
FIG. 3 is a cross-sectional view taken along line 3—3 of FIG. 2.

The transport equipment and rotating mechanism carries the tube over a source of diffused light. The source can include a conventional source of bright light 17 and a translucent panel 18. The panel 18 is disposed beneath the conveyor 11 and abuts relatively dark non-reflective panels 20 along the path of travel of the conveyor. The panels 18 and 20 are split or slotted such that the lower edges of the conveyor or chains 12 extend therethrough. The panel 18 scatters the light generated by the light source so as to illuminate the tube 10 with light which is rich in angular content. To ensure that the longitudinal axis of the tube remains generally perpendicularly aligned to the direction of its movement, a side rail 22 can be provided to abut one end of the tube 10 and maintain it in alignment. A side rail (not shown) can be provided on the other side of the panels 18 and 20 to assist in the alignment of the tube 10. A translucent side panel 24 is included in the inspection area which can scatter the light from a second source 25 (FIG. 3) so as to provide additional diffuse illumination of the tube 10. The importance of brightly illuminating the tube 10 with diffused light will be explained below.

As the tube 10 is moved through the inspection area, light passing through the translucent panels 18 and 24 is reflected from the tube 10 in all directions. A camera system 26 is positioned above the conveyor 11 to receive a portion of that reflected light. The camera system 26 can include a linear diode array 28 which is oriented generally parallel to the longitudinal axis of the tube 10. The diode array 28 is composed of a plurality of light-sensitive diodes, each of which generates an electrical signal proportional to the intensity of light received thereon. A linear segmented diode array was selected to improve the signal to noise ratio. The diodes in the array 28 can be sequentially scanned to provide a signal representing the amount of light received from a longitudinally extending portion of the tube 10 under inspection.

In this embodiment, the diode array was chosen to provide an inspection field height of about 0.017 inches at the image plane of the camera. Thus, the diodes are "tall" or "wide" diodes with a height of about 0.017 inches. Utilizing such an array, a lens having a demagnification factor of eleven can be utilized such that the effective inspection field width at the tube 10 is approximately 0.187 inch (dimension "W" in FIG. 2) resulting in a projected field width of approximately 0.55 inch (dimension "P" in FIG. 2) in a plane tangent to the top of the tube 10. The conveyor 11 can move the tube 10 through the inspection area at a velocity of one hundred eighty-eight inches per minute while the rotating mechanism rotates the tube 10 approximately nine hundred times each minute. At these velocities, the tube 10 will be moved approximately 0.209 inch in the time it takes for it to be rotated one complete revolution. Good results have been obtained by positioning the camera means 26 above the conveyor 11 looking down at approximately a 20° angle. Thus, a portion of the upper half of the tube 10 is imaged onto some part of each diode in the array 28 for the entire time it takes to make one revolution. If the camera system 26 electronically scans over the diode array 28 at intervals of four hundred fifty microseconds, then the tube 10 will be inspected at intervals of approximately 2.4° of rotation and a given point on the tube may be inspected an average of thirty times at different angular orientations before being moved out of the field of inspection.

It is well known that a defect in a glass container, such as a fire check 32 in the tube 10, will produce a mirror-like reflection when light is shined upon it. Thus, when light is reflected from the check 32 to the diode array 28, the resulting electrical signal will be greater than when a non-defective portion of the tube 10 is inspected. Typically, the checks are generally perpendicular to the outer surface of the wall of the tube. However, in order to assure that the diode array 28 receives sufficient light reflected by a check 32 having arbitrary location and orientation within the tube 10, the illumination of the tube 10 must be broad in extent and rich in angular subtense at any given inspection site. The large area of the source of diffused light also increases the angular extent of rotation of the tube 10 during which the check 32 will pass through a favorable orientation to reflect light from the source of diffused light into the relatively unidirectional viewing aspect of the camera 28. In addition the tube must remain in the field of view of the camera during the time the tube makes at least one revolution. This is achieved in this invention by choosing diodes which are 0.017 inch high and viewing with the camera from a point approximately 20° above the path of travel of the tube. In order to increase the reliability of check detection, the side panel 24 is included. The light scattered from the side panel 24 will be reflected from a check that is circumferential in orientation and, therefore, would be less likely to reflect sufficient light from the panel 18 to be detected.

Referring to FIG. 2, the camera system 26 includes means for longitudinally scanning the tube 10 to measure the amount of light reflected therefrom and generating an electrical output signal proportional in amplitude to the amount of light received. The output signal is transmitted on signal line 34 to a conventional signal averaging and holding means 36 and one input of a conventional comparing means 38. The output signal V(r) from the signal averaging and holding means is added to a predetermined voltage V(p) in a conventional summing amplifier 40 to generate the threshold signal V(t) which is applied to the other input of the comparing means 38. When the amplitude of the camera output signal exceeds the amplitude of the threshold signal, the comparing means 38 generates a reject signal which is transmitted on a line 42.

Figure 4:
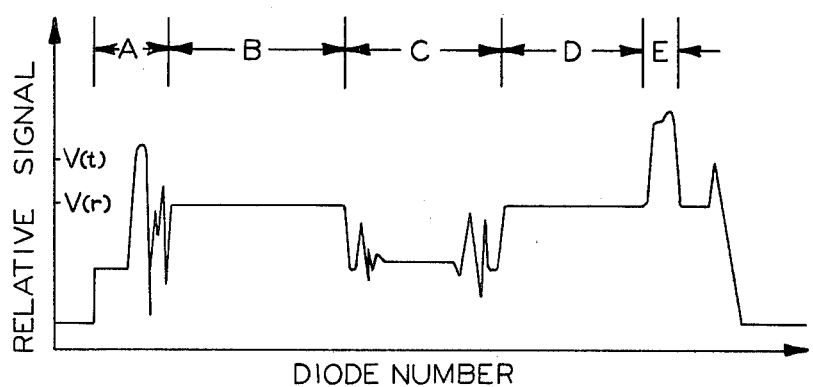
FIG. 4 is a sample wave form of one scan of the check detector of FIG. 1.

Referring now to FIG. 4, there is illustrated a sample scanning signal of one longitudinal scan of a piece of tubing as generated by the diode array 28. The signal has been divided into five regions to aid in clearly explaining the graph. The output wave form in Region A represents the signal corresponding to the end of a piece of tubing having a special configuration and, consequently, is rather erratic. Region B represents the signal from the inspection of the smooth cylindrical portion of the tube 10, such portion containing no defects. It will be appreciated that the signal in Region B is relatively smooth and constant throughout the length of the tube 10. Region C represents the signal from the portion of the tube 10 which is above the transport means. Hence, the relative signal in Region C will be different than that in Region B because the chains 12, lugs 14 and the belt 16 will block out a portion of the light shining on the tube 10 from the translucent panel 18. However, extraneous light reflected from the transport means may cause a higher output signal than that from Region B. Region E represents the signal relating to that portion of the tube 10 containing the fire check 32. As explained above, the check 32 reflects light from the source directly to the camera 26, causing the diode array 28 to generate a higher amplitude signal. The Region D between Regions C and E is similar to Region B and the region beyond Region E represents the light that would be received from a smooth end of the tube. However, this is only representative of one of several combinations of special and smooth ends.

It will be appreciated that the length of each sweep of the diode array 28 covers a longitudinal inspection area which exceeds the length of the tube 10. Since it is desired only to inspect that portion of the tube 10 having smooth cylindrical surfaces, characterized in Region B by the generally uniform amplitude signal obtained therefrom, those portions of the scanned signal which relate to a special end of the tube 10, as shown in Region A, can be eliminated by conventional electronic masking techniques. Similarly, the signal from the glazed end of the tube 10 can also be ignored. It may further be desirable to mask out Region C to avoid any false rejections caused by the transport equipment. Since Region C will always be near the center of the tube 10, it is unlikely that any checks caused by the cutting of the ends of the tube 10 will be present in that center area without being detected elsewhere.

Region B represents a generally constant baseline signal resulting from the reflections of the diffused source by the cylindrical surface of the tube 10. The signal is generally uniform across the portion of the tube 10 being inspected for a particular scan of the camera 26. However, this signal will vary from scan to scan. The baseline changes can be caused by circumferential variations in the tubes, light source variations, and camera vibration as well as other factors. For this reason, it is desirable to compare the check signal, as shown in Region E, against a threshold level which is referenced to the constant baseline signal for that particular scan. The reference voltage, such as that indicated by V(r) in FIG. 4, can be electronically determined by averaging a first portion of the scanning signal. The first few diode detector elements in Region B for each camera scan can provide the signals to be averaged. Taking into account slight circumferential variations in the tubes being inspected, the nonuniformity of the light source, vibration of the camera and the variation in the amount of light reflected by the tube as it passes through the inspection zone, the reference voltage V(r) will vary from tube to tube and from scan to scan as the tube moves over the light source.

The threshold voltage, such as that indicated by V(t) in FIG. 4, can be obtained by adding a small predetermined constant voltage signal to the reference voltage V(r) to account for slight intrascan variations and provide adjustment of sensitivity to defects. Thus, it will be appreciated that the threshold voltage V(t) will vary with the reference voltage V(r) from tube to tube and scan to scan. Any conventional comparing means can be utilized to compare the scanning signal against the threshold voltage V(t). A signal which exceeds the threshold voltage V(t) on a given scan indicates that a check defect is present in the tube under inspection. A reject signal can be generated by conventional means to a rejection unit located downstream of the inspection area for rejecting the particular defective tube.

Although the baseline amplitudes in Regions B and D are generally similar, they can be different. The first few diode detector elements in each region can then be used to provide the signals to be averaged for a separate reference for each region. A second predetermined constant voltage, different from that of Region B, may be added to the Region D reference to provide a threshold signal for Region D which has a different defect sensitivity than Region B. Although only two inspection regions have been shown, the present invention can be utilized with additional inspection regions having different baseline amplitudes and/or different threshold signal levels.

In accordance with the provisions of the patent statutes, the principle and mode of operation of the present invention have been explained and illustrated in its preferred embodiment. However, it must be appreciated that the invention can be practiced otherwise than as specifically explained or illustrated without departing from its spirit or scope.

What is claimed is:

1. A method of inspecting a plurality of glass tubes for checks comprising the steps of:
  a. rotating each of the tubes about its longitudinal axis;
  b. moving said rotating tubes in sucession laterally through an inspection area in a direction generally perpendicular to its longitudinal axis;
  c. illuminating the tubes with a diffuse source of light in the inspection area;
  d. positioning a linear diode array at an angle of approximately 20° above the tubes with the longitudinal axis of said diode array generally parallel to the longitudinal axes of the tubes;
  e. imaging a plurality of longitudinally extending portions of the tubes in the inspection area on said diode array;
  f. scanning said diode array; and
  g. generating an electrical output signal proportional to the amount of light received from the tubes during each scan.

2. In an apparatus for inspecting a plurality of glass tubes for checks in an inspection area comprising:
  a rotating mechanism for rotating the tubes about their longitudinal axes, transport equipment for moving the tubes in a direction generally perpendicular to their longitudinal axes in spaced apart fashion through an inspection area,
  a source of diffuse light in the inspection area for illuminating the tubes, a linear diode array positioned at an angle of approximately 20° above the path of travel of the tubes and parallel thereto, means for imaging the longitudinal extent of the tubes in the inspection area on the diode array, and means to scan the array to measure the amount of light reflected from the tubes.

3. A method of inspecting a glass tube for checks comprising the steps of: rotating the tubes about its longitudinal axis while moving said tube through an inspection area in a direction generally perpendicular to its longitudinal axis, positioning a linear diode array having a predetermined inspection field height with its longitudinal axis generally parallel to the longitudinal axis of the tube, positioning said diode array at an angle of approximately 20° above the path of travel of the tube whereby the effective inspection field width at the tube is sufficient to include at least the entire region traversed by the tube during one revolution of the tube, and scanning the output of said diode array as an index of the presence of a defect in the tube.

4. A method of inspecting a glass tube in accordance with claim 3 including a step of inspecting a plurality of glass tubes with said diode array.

5. An apparatus for inspecting a glass tube for optical checks comprising:

means engaging the tube for simultaneously rotating the tube about its longitudinal axis and moving the tube through an inspection area in a direction generally perpendicular to its longitudinal axis, a source of diffuse light in the inspection area for illuminating a portion of the tube; and camera means for viewing the illuminated portion of the tube in the inspection area and to measure the amount of light reflected therefrom; including a linear diode array having a predetermined inspection field height positioned at an angle of approximately 20° above the path of travel of the tube whereby the effective inspection field width in the inspection zone is sufficient to include at least the entire region traversed by the tube during one revolution of the tube.

6. Apparatus for inspecting a plurality of glass tubes for optically reflective defects comprising:

means engaging the tubes for simultaneously rotating the tubes about their elongated axis and moving the tubes in spaced apart succession at right angles to its axis through an inspection zone, means at said inspection zone for illuminating said tube through substantially its full length and the full width of the inspection zone, camera means providing an image of the full length of said tube and the width of the inspection zone, said camera means including a linear diode array extending parallel to the longitudinal axis of said tube with means for focusing the image on the diode array, and, means for scanning said diode array to provide an indication of a defect in said tube.

7. The apparatus of claim 6 wherein said means for illuminating said tubes comprises a broad source of diffused light.

8. An apparatus for inspecting a plurality of glass tubes in accordance with claim 7 wherein said broad source of diffused light includes a translucent panel between said light source and the tubes in the inspection area.

9. An apparatus for inspecting a plurality of glass tubes in accordance with claim 8 wherein said panel is positioned in a plane substantially parallel to the path of travel of the tubes.

10. An apparatus for inspecting a plurality of glass tubes in accordance with claim 9 including a second source of light and a second translucent panel positioned between said second source and the tubes in the inspection area.

11. The apparatus of claim 9 further including a second means at said inspection station for illuminating the tube in the axial direction.

* * * * *